United States Patent
Kashiwagi et al.

(10) Patent No.: US 6,410,535 B1
(45) Date of Patent: *Jun. 25, 2002

(54) PROPHYLACTIC OR THERAPEUTIC AGENTS FOR DISEASES HAVING VASCULAR DYSFUNCTION ASSOCIATED WITH INSULIN RESISTANCE

(75) Inventors: Atsunori Kashiwagi; Kazuya Shinozaki; Yoshihiko Nishio; Tomio Okamura, all of Shiga-ken; Noboru Toda; Ryuichi Kikkawa, both of Osaka, all of (JP)

(73) Assignee: Suntory Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,579

(22) Filed: Oct. 27, 1999

Related U.S. Application Data

(63) Continuation of application No. PCT/JP99/00917, filed on Feb. 25, 1999.

(30) Foreign Application Priority Data

Feb. 27, 1998 (JP) ............................................ 10-047720

(51) Int. Cl.[7] ............................................ A61K 31/495
(52) U.S. Cl. ........................................ 514/249
(58) Field of Search ........................................ 514/249

(56) References Cited

U.S. PATENT DOCUMENTS

| | | |
|---|---|---|
| 4,665,182 A | 5/1987 | Nichol et al. |
| 4,758,571 A | 7/1988 | Curtius et al. |
| 4,774,244 A | 9/1988 | Curtius et al. |
| 4,778,794 A | 10/1988 | Naruse et al. |
| 5,753,656 A | 5/1998 | Sakai et al. |

FOREIGN PATENT DOCUMENTS

| | | |
|---|---|---|
| EP | 108890 A | 5/1984 |
| EP | 209689 A | 1/1987 |
| JP | 59-25323 | 2/1984 |
| JP | 59076086 | 4/1984 |
| JP | 61277618 | 12/1986 |
| JP | 267781/88 | 11/1988 |
| JP | 63267781 | 11/1988 |
| JP | 06 056669 | 3/1994 |

OTHER PUBLICATIONS

Walter et al., Inhalation Of The Nitric Oxide Synthase Cofactor Tetrahydrobiopterin In Volunteers. Amer J. Respir & Crit Care Med., 1997, p 2009.

Wever et al., Tetrahydrobiopterin Regulates Superoxide And Nitric Oxide GENERATION Recombinant Endothelial Nitric Oxide Synthase, Biochem Biophys Res, 1997, pp 340–344.

Prast et al., Effects of Sepiapterin Treatment On Tetrahydrobiopterin Levels And Blood Pressure In Spontaneously Hypertensive Rats, Biology of Nitric Oxide, 1992, pp 10–12.

Pinkney et al, endothelial dysfunction:causes of the insulin resistance syndrome, Diabetes Sep. 1997, PS12.

Higashi et al. Relationship between insulin resistance and endothelium dependent vascular Relaxation in patients with essential hypertension, Hypertension, Jan. 1997, p 284.

Shinozaki et al., "Insulin Resistance . . . ", Circulation 1995, vol. 92: p 1749–1757.

Shinozaki et al., "Demonstration of Insulin . . . ", Diabetes Care 1996, vol. 19: p 1–7.

Shinozaki et al., "Role of Insulin Resistance . . . ", Stroke 1996 vol. 27 p 37–43.

Shinozaki et al., "Insulin . . . ", Arterioscler, Thromb. Vasc.Biol., 1997 vol. 17: p 3302–3310.

Law et al., "Troglitazone Inhibits . . . ", J. Clin. Invest. 1996, vol. 98: p 2546–2551.

Tardif et al., "Probucol and Multivitamins . . . ", N. Eng. J. Med. 1997, vol. 337: p 365–372.

Hwang et al., "Fructose–Induced Insulin . . . ", Hypertension 1987, vol. 10: p 512–516.

(List continued on next page.)

*Primary Examiner*—Raymond Henley, III
(74) *Attorney, Agent, or Firm*—Manelli Denison & Selter PLLC; Paul E. White, Jr.

(57) ABSTRACT

It is an object of the present invention to provide a pharmaceutical composition for effectively preventing or improving diseases having vascular dysfunction associated with insulin resistance. The present invention provides pharmaceutical compositions for preventing or treating diseases having vascular dysfunction associated with insulin resistance, comprising as an active ingredient a compound of the formula (I):

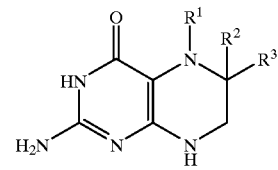

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represents a single bond, or a pharmaceutically acceptable salt thereof.

9 Claims, No Drawings

OTHER PUBLICATIONS

Ohara et al., "Hypercholesterolemia . . . ", J. Clin. Invest. 1993, vol. 91: p 2546–2551.

Rees et al., "Nitric Oxide and the Regulation . . . ", Hypertension 1996, vol. 28: p 367–371.

Toda et al., "Endothelial Modulation of . . . ", Stroke 1993, vol. 24: p 1584–1588.

Palmer et al., "Nitric oxide release accounts for . . . ", Nature 1987, vol. 327: p 524–526.

Kwon et al., "Reduced Biopterin as . . . ", J. Biol. Chem., 1989, vol. 264: p 20496–20501.

Jap. J. Pharmacology, 75 (1997) Suppl. 1, 11p.

Gibbons et al., "Molecular Therapies For Vascular Diseases", Science, vol. 272, May 3, 1996, pp 689–693.

U.S. patent application Ser. No. 09/069,102, Ishihara et al., filed Jan. 12,1999.

U.S. patent application Ser. No. 09/472,550 , Okamura et al., filed Oct. 27, 1999.

PROPHYLACTIC OR THERAPEUTIC AGENTS FOR DISEASES HAVING VASCULAR DYSFUNCTION ASSOCIATED WITH INSULIN RESISTANCE

This is a Continuation of: PCT/JP99/00917 filed Feb. 25, 1999.

This is a continuation of PCT/JP98/00917 filed Feb. 25, 1998.

BACKGROUND OF THE INVENTION

The present invention relates to pharmaceutical compositions for preventing and/or treating diseases having vascular dysfunction associated with insulin resistance, comprising as an active ingredient a compound of the formula (I):

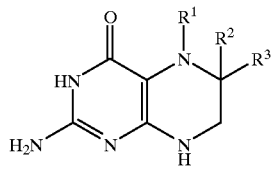

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represents a single bond, or a pharmaceutically acceptable salt thereof.

Insulin resistance is a pathologic state observed in patients with type II diabetes and typically characterized by a lack of lowering of blood glucose level even under a high insulin state. Recently, a pathologic state characterized by a complication of abnormal glucose tolerance, obesity, hypertension and hyperlipidemia in one individual was reported and named insulin resistance syndrome, syndrome X or offal fat syndrome. Large-scale epidemiological studies showed that these pathologic states are basically associated with insulin resistance and may be a hazardous factor in various arteriosclerotic diseases. Consequently, it is clinically important to explain and prevent these states.

We have clinically examined the role of insulin resistance in vascular endothelial dysfunction and an advanced state thereof, such as arteriosclerotic process as well as various arteriosclerotic diseases. We first found that marked hyperinsulinemia independent from other hazardous factors, i.e. insulin resistance also occurs in diseases other than diabetes such as non-diabetic coronary vasoconstrictive angina (Shinozaki, K. et al., Circulation 1995, 92: 1749–1757). We also showed the presence of marked insulin resistance in effort angina or cases having significant constrictive lesion In cerebral angiography (Shinozaki, K. et al., Diabetes Care 1996, 19: 1–7; Shinozaki, K. et al., Stroke 1996, 27:37–43). Furthermore, we also showed the presence of insulin resistance and initial arteriosclerosis in vivo (Shinozaki, K. et al., Arterioscler. Thromb. Vasc. Biol., 1997, 17: 3302–3310).

Vascular endothelium has been known to play an important role in vascular tonus or thrombopoiesis, and in 1980, the presence of endothelium-derived relaxing factor (EDRF) was first reported. The entity of EDRF was proved to be nitric oxide (NO) in 1987. NO is a gaseous radical and has been shown to readily pass through cell membranes and exert a wide variety of effects such as circulation control, neurotransmission, inhibition of platelet aggregation, antibacterial or anticancer effect. NO not only controls metabolism by reacting with heme enzyme or SH enzyme groups, but also has physiological functions and pathological activity by crosstalking with active oxygen species such as superoxide ($O_2^-$), SH compounds, ascorbic acid or the like. However, its in vivo molecular entity is still unknown in many respects because all of these molecules are unstable.

NO having a wide variety of effects as described above is produced when L-arginine is oxidized from $N^G$-hydroxyl-L-arginine into L-citrulline and the reaction is catalyzed by an enzyme called NO synthase (NOS). NOS widely occurs in the vascular endothelium, nervous system, kidney, platelets, cardiac muscles, smooth muscles, etc. and the gene therefor has already been cloned and structurally analyzed. As a result, the gene for NOS was found to contain a binding site for (6R)-L-erythro-5,6,7,8-tetrahydrobiopterin (hereinafter referred to as "BH4") included in compounds of the formula (I) as active ingredients of the present invention, in addition to those for coenzymes such as calmodulin (CaM), flavin, NADPH. Moreover, BH4 has been suggested to actually be involved in control of the function of NOS.

We examined the in vivo influence of a high insulin state on superoxide production and endothelium-dependent vasorelaxing ability, on the hypothesis that vascular tonus abnormality and vascular endothelial cell disorder might be caused by increased production of active oxygen species in insulin resistant state. The result showed that some mechanism hinders activation of NOS in insulin resistant state while NOS is activated in the vascular endothelium to maintain the vasorelaxing ability in an exogenous high insulin state induced by externally administering insulin. This suggests that the presence of superoxide may be excessive on vascular walls due to a decrease of NO resulting in an acceleration of arteriosclerosis and enhancement of vasoconstriction in insulin resistant states (Shinozaki, K., Kashiwagi, A. et al. : Superoxide anion impairs endothelium-dependent vascular relaxation in insulin resistant rat aortas. Jap. J. Pharmacology 75 (1997) suppl. 1, p. 11).

Thus, the relationship between insulin resistant states and endothelial dysfunction has been posited. Various studies have been made on drugs for improving vascular dysfunction caused by insulin resistance to prevent or treat various diseases associated therewith and thiazolidine dione derivatives were mentioned as candidates therefor (Law, R. E. et al., Troglitazone inhibits vascular smooth muscle cell growth and intimal hyperplasia, J. Clin. Invest. 98: 1897, 1996). However, no definite conclusion has yet been reached.

Recent investigations of various vascular diseases at a molecular level have led to a therapeutic strategy directed to blood vessels such as endothelial cells. And it is considered that one of the most promising therapies is to treat blood vessels with an agent which controls production of the entity of EDRF, i.e. NO, or an agent which has an antioxidant action (Gibbons, G. H., Dzau, V. J., Science. Vol. 272, 689–693, 1996). For example, antioxidant agents such as vitamins E or probucol are expected to resist oxidative stress in coronary arteriorestenosis known to be caused by the metabolite having an oxidant action following percutaneous transluminal coronary angioplasty (PTCA) or coronary artery bypass grafting (CABG) (Tardif, J. C. et al.: N. Eng. J. Med. 1997, 337: 365–372), and nitrate agents such as nitroglycerin preparations are used as exogenous NO donors for therapy of angina. However, no drug or therapy that satisfies this therapeutic strategy has yet been established.

The purpose of therapy is to prevent complications of the vascular system caused by insulin resistance so that patients may enjoy a prolonged and higher quality of life. This requires lifelong management by long-term pharmacotherapy. In spite of various studies on therapeutic agents for insulin resistance as described above, no drug exists at present that is completely satisfactory in terms of side effects, safety during long- term use and improvement in QOL (quality of life). Thus, the development of therapeutic agents satisfying truly desirable conditions is in great demand.

The compounds of the formula (I) as active ingredients in pharmaceutical compositions of the present invention are known compounds for use in pharmaceutical compositions against malignant hyperphenylalaninemia, depression, Parkinson's disease, etc. For example, see Japanese Patent Public Disclosure (KOKAI) Nos. 25323/84, 76086/84, 277618/86 and 267781/88.

SUMMARY OF THE INVENTION

It is an object of the present invention to provide a safe pharmaceutical composition for diseases having vascular dysfunction associated with insulin resistance without side effects, which prevents the progress of conditions, prevents the progress of complications and improves the quality of life of patients.

We, the inventors, hypothesized about therapy for diseases having vascular dysfunction associated with insulin resistance that endothelial dysfunction caused by insulin resistant state might be improved by controlling both of increased production of active oxygen species and decreased production of NO to normalize each of them. As a result of careful studies to improve endothelium-dependent vasorelaxation, we unexpectedly found that BH4, which is a coenzyme for NOS, improves decreased production of endogenous NO and also suppresses increased production of active oxygen species in insulin resistant state to significantly improve lowered endothelium-dependent vasorelaxation. Thus, we discovered the effect of BH4 in improving vascular dysfunction in insulin resistant states, and as a result accomplished the present invention.

The present invention relates to an effective therapy with BH4 preparations for diseases having vascular dysfunction associated with insulin resistance.

DETAILED DESCRIPTION OF THE INVENTION

The present invention relates to a pharmaceutical composition for preventing or treating diseases having vascular dysfunction associated with insulin resistance, comprising as an active ingredient a compound of the formula (I):

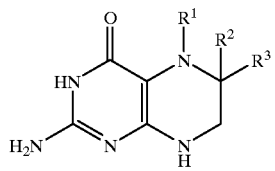

wherein $R^1$ and $R^2$ each represents a hydrogen atom or taken together with each other represent a single bond, while $R^3$ represents $-CH(OH)CH(OH)CH_3$, $-CH(OCOCH_3)CH(OCOCH_3)CH_3$, $-CH_3$, $-CH_2OH$ or a phenyl group when $R^1$ and $R^2$ each represents a hydrogen atom, or $-COCH(OH)CH_3$ when $R^1$ and $R^2$ together represents a single bond, or a pharmaceutically acceptable salt thereof.

As used herein, the term insulin resistance means a pathologic state where enhancement of peripheral sugar assimilation by normally secreted insulin declines, while suppression of the glucose level released from the liver declines to induce abnormal glucose tolerance and suppression of lipolysis by insulin also declines. Characteristically, it often presents with hyperinsulinemia, but it is not always the case. Insulin resistance has been reported to occur in not only insulin-sensitive cells but also vascular wall cells. Diseases having vascular dysfunction associated with insulin resistance include those caused by insulin resistance, those aggravated by insulin resistance, those for which cure is retarded by insulin resistance, etc., such as hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases or the like so far as they are associated with insulin resistance.

When administered to patients with these diseases, BH4 can prevent or treat these diseases by activating the functions of NOS, increasing NO production and suppressing the production of active oxygen species to improve disorders of vascular endothelial cells.

Accordingly. the treatment or prevention according to the present invention is directed to insulin resistant diseases associated with vascular dysfunction having vascular tonus abnormality or endothelial dysfunction.

Compounds of the formula (I) as active ingredients of the present invention include the following ones and pharmaceutically acceptable salts thereof:

(6R)-L-erythro-5,6,7,8-tetrahydrobiopterin (BH4)

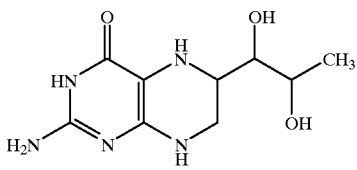

(6R,S)-5,6,7,8-tetrahydrobiopterin,
1',2'-diacetyl-5,6,7,8-tetrahydrobiopterin

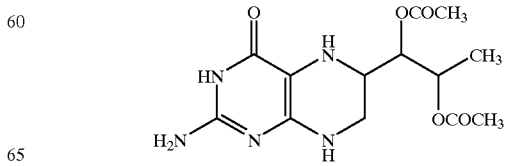

sepiapterin

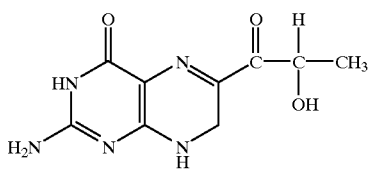

6-methyl-5,6,7,8-tetrahydropterin

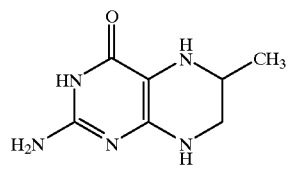

6-hydroxymethyl-5,6,7,8-tetrahydropterin

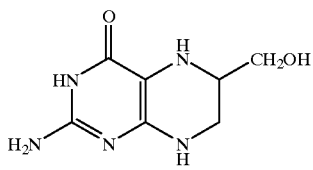

6-phenyl-5,6,7,8-tetrahydropterin

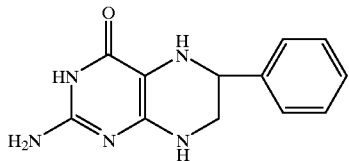

Among aforementioned compounds, 5,6,7,8-tetrahydrobiopterins or salts thereof are preferable, and BH4 or salts thereof are the most preferable.

Compounds of the formula (I) used as active ingredients in the present invention are known compounds. For example, see Japanese Patent Public Disclosure (KOKAI) Nos. 25323/84, 76086/84, 277618/86 and 267781/88. These compounds may be used as appropriate salts with pharmacologically non-toxic acids, including mineral acids such as hydrochloric acid, phosphoric acid, sulfuric acid, boric acid; and organic acids such as acetic acid, formic acid, maleic acid, fumaric acid, mesylic acid.

Pharmaceutical compositions of the present invention are effective against the above-mentioned diseases. For example, they are effective against, but not limited to, hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases or the like so far as they are associated with insulin resistance.

Pharmaceutical compositions of the present invention are prepared by formulating a compound of the formula (I) with a pharmaceutically common carrier by conventional procedures into a dosage form suitable for oral, rectal or parenteral administration (including administration into the vein and cerebrospinal fluid).

The carrier used for these pharmaceutical formulations generally includes excipients, binders, disintegrators, etc. depending on the dosage form chosen.

Typical examples of excipients include starch, lactose, sucrose, glucose, mannitol, cellulose, and examples of binders include polyvinylpyrrolidone, starch, sucrose, hydroxypropylcellulose and Arabic gum. Examples of disintegrators include starch, agar, gelatin powder, cellulose, CMC, but any other conventional excipients, binders and disintegrators may also be used.

In addition to such carriers, pharmaceutical compositions of the present invention may also contain antioxidants for stabilizing active ingredients. Antioxidants can be appropriately selected from those commonly used for pharmaceutical preparations, such as ascorbic acid, N-acetylcysteine, L-cysteine, dl-α-tocopherol, natural tocopherol, etc. They are used in an amount that stabilizes (one or more) active ingredients, and generally they are preferably used in the ratio of 0.2 to 2.0 parts by weight to 1 part by weight of the active ingredient(s).

Formulations of the present invention suitable for oral administration may be provided in the form of tablets, sublingual tablets, capsules, powders, granules or fine granules, or suspensions in a non-aqueous liquid such as emulsions, potions or syrups, that contain the prescribed amount of (one or more) active ingredients.

For example, granules are prepared by homogeneously mixing (one or more) active ingredients with one or more auxiliary ingredients such as carriers and antioxidants as mentioned above, followed by granulation and sieving to uniform grain size. Tablets can be prepared by compacting or molding (one or more) active ingredients optionally with one or more auxiliary ingredients. Capsules are prepared by filling powder or granules of (one or more) active ingredients optionally mixed homogenously with one or more auxiliary ingredients into appropriate capsules using a capsule filling machine or the like. Formulations for renal administration can be provided as suppositories using conventional carriers such as cacao butter. Parenteral formulations can be provided as dry solids of (one or more) active ingredients sealed in a nitrogen-filled sterilized container. Such dry solid preparations can be administered to patients by dispersing or dissolving them into a determined amount of sterilized water just prior to administration.

These formulations may preferably be prepared by incorporating antioxidants as mentioned above optionally with one or more auxiliary ingredients selected from buffers, flavors, surfactants, thickeners, lubricants, etc. in addition to active ingredients and ordinary carriers.

The dosage of active ingredients, i.e. compounds of the formula (I) may naturally vary with the administration route, the symptom to be treated and the particular patient, and may be ultimately determined by an attendant physician.

For example, an appropriate dosage for treating diseases having vascular dysfunction associated with insulin resistance depends on the purpose of administration, the age, weight, condition of the patient, etc., but ranges from 0.1 to 50 mg/kg (body weight)/day, typically 0.5 to 10 mg/kg (body weight)/day for oral administration.

A desired dosage of said active ingredients may be administered once a day or may be administered in divided doses of two to four times a day at appropriate intervals.

Active ingredients may be administered alone without being mixed with other ingredients, or in combination with pharmaceutical formulations containing other active ingredients suitable for the disease under treatment to facilitate control of the dosage, for example.

In addition to compounds of the formula (I) as active ingredients, formulations of the present invention may contain at least one auxiliary active ingredient selected from the group consisting of substrates or coenzymes or cofactors for NOS such as L-arginine, flavins (for example, FAD, FMN, etc.) and calcium. More excellent therapeutic effects can be expected when compounds of the formula (I) are mixed with these active ingredients than when used alone. The proportion of each of said auxiliary active ingredients in formulations of the present invention is not specifically limited. For example, the weight ratio of at least one selected from L-arginine, flavins and calcium to 1 part by weight of the compounds of the formula (I) may be within the range from 0.1 to 10, preferably 0.5 to 2.

For example, an appropriate dosage of such mixed formulations for treating diseases having vascular dysfunction associated with insulin resistance depends on the purpose of administration, the age, weight, condition of the patient, etc., but ranges from 0.1 to 50 mg/kg (body weight)/day, preferably 0.5 to 10 mg/kg (body weight)/day in terms of the total amount of active ingredients for oral administration.

A physician may appropriately choose formulations containing compounds of the formula (I) alone or in combination with other active ingredients, depending on the age, condition or other factors of the patient.

The most preferable active ingredients used in the present invention are (6R)-L-erythro-5,6,7,8-tetrahydrobiopterin (BH4) and salts thereof, but their analogues such as (6R,S)-5,6,7,8-tetrahydrobiopterin, 1',2'-diacetyl-5,6,7,8-tetrahydrobiopterin, sepiapterin, 6-methyl-5,6,7,8-tetrahydropterin, 6-hydroxymethyl-5,6,7,8-tetrahydropterin or 6-phenyl-5,6,7,8-tetrahydropterin and salts thereof may also be used. Needless to say, however, BH4 naturally occurring component in living bodies is preferable. BH4 dihydrochloride exhibits little toxicity in rats as shown by the acute toxicity of 2 g/kg (body weight) or more via oral route. An optically inactive analogue, (6R,S)-5,6,7,8-tetrahydrobiopterin is also only slightly toxic as reported in Japanese Patent Public Disclosure No. 25323/84 for the treatment of Parkinson's disease, so that it can also be used for the therapy according to the present invention. Other compounds of the formula (I) also exhibit little or no acute toxicity.

The following examples further illustrate the present invention in detail without, however, limiting the same thereto.

EXAMPLES

Example 1
Granules and Fine Granules

To 1 part (by weight) of polyvinylpyrrolidone (Kollidon 30) dissolved in sterilized purified water were added 10 parts of ascorbic acid and 5 parts of L-cysteine hydrochloride to give a homogeneous solution, and then 10 parts of BH4 dihydrochloride were added to prepare a homogeneous solution.

This solution was added to 59 parts of an excipient (mannitol or lactose) and 15 parts of a disintegrator [corn starch or hydroxypropylcellulose (LH-22)], and the mixture was kneaded, granulated, dried, then sieved.

Example 2
Tablets

The homogeneous solution of an active ingredient prepared in Example 1 was mixed with 58 parts of lactose and 15 parts of microcrystalline cellulose, then with 1 part of magnesium stearate and tableted.

Example 3
Capsules

The dosage form prepared in Example 1 was filled into capsules. However, the formulation further contains 0.2% of magnesium stearate as a lubricant.

Example 4
Injection

| | |
|---|---|
| BH4 dihydrochloride | 1.5 g |
| Ascorbic acid | 1.5 g |
| L-cysteine hydrochloride | 0.5 g |
| Mannitol | 6.5 g |

The above ingredients were dissolved into sterilized purified water to make 100 ml and sterilized, and each of 1 ml or 2 ml aliquot was dispensed into a vial or ampule, then lyophilized and sealed.

Example 5
Injection

A solution of 2.0 g of BH4 dihydrochloride dissolved in sterilized purified water to make 100 ml under an anaerobic atmosphere was sterilized and sealed in the same way as in Example 4.

Example 6
Suppositories

| | |
|---|---|
| BH4 dihydrochloride | 150 parts |
| Ascorbic acid | 150 parts |
| L-cysteine hydrochloride | 50 parts |

The above ingredients were homogeneously ground and dispersed into 9950 parts of cacao butter.

Example 7
Granules

| | |
|---|---|
| H4 dihydrochloride | 5 parts |
| Ascorbic acid | 5 parts |
| L-cysteine hydrochloride | 2 parts |

The above ingredients were used to prepare a homogeneous solution.

This solution was added to a homogeneous mixture of 55 parts of mannitol, 1 part of polyvinylpyrrolidone, 14 parts of hydroxypropylcellulose and 5 parts of L-arginine or calcium, and the mixture was kneaded, granulated, dried, then sieved.

Example 8
Granules

| | |
|---|---|
| BH4 dihydrochloride | 5 parts |
| Ascorbic acid | 5 parts |
| L-cysteine hydrochloride | 5 parts |
| Mannitol | 52 parts |

-continued

| | |
|---|---|
| Polyvinylpyrrolidone (Kollidon 30) | 1 part |
| Hydroxypropylcellulose (LH-22) | 12 parts |
| L-arginine or calcium | 10 parts |

The above ingredients were granulated and sieved in the same way as in Example 7.

Example 9

Granules

| | |
|---|---|
| BH4 dihydrochloride | 5 parts |
| Ascorbic acid | 5 parts |
| L-cysteine hydrochloride | 2 parts |

The above ingredients were used to prepare a homogeneous solution.

This solution was added to a homogeneous mixture of 10 parts of L-arginine or calcium, 50 parts of mannitol, 1 part of polyvinylpyrrolidone (Kollidon 30) and 9 parts of hydroxypropylcellulose (LH-22), and the mixture was kneaded, granulated, dried, then sieved.

Example 10

Male Sprague-Dawley rats (150 g, supplied from Charles River) were used to prepare a model group with insulin resistance induced by fructose feed loading (hereinafter referred to as "FR group") according to the procedure described by Hwang et al. (Hwang, I-H. et al., Hypertension 10:512, 1987). A control group grown with a starch feed (hereinafter referred to as "CTR group") was also prepared (FR group: n=16; CTR group: n=16). FR group received a feed containing 67% (hereinafter meaning % by weight) carbohydrate (containing 98% fructose available from Oriental Yeast Co., Ltd.), 13% fat and 20% protein, while CTR group received a feed containing 58% carbohydrate, 12% fat and 30% protein. Ten mg of BH4 dihydrochloride/kg (body weight)/day was orally administered to 8 animals of each of FR group and CTR group (designated as "FR+BH4 groups" and "CTR+BH4 group", respectively). After 8 weeks, the thoracic aorta was collected. For each group, endothelium-separated sections (EC (−)) and non-separated sections (EC (+)) were prepared and examined for superoxide anion ($O_2^-$) production level, endothelial NOS (eNOS) activity and endothelium-dependent vasorelaxation.

Statistics

Group-to-group statistic analyses were made by one-way ANOVA, with the significance level being $p<0.05$. Multiple comparison was made by Bonferronl/Dunn, with the significance level being $p<0.05$.

Superoxide anion ($O_2^-$) production level in thoracic aorta tissue sections

Measurement of $O_2^-$ production level was made by the lucigenin-enhanced chemiluminescence method (Ohara et al., J. Clin. Invest. 91: 2546, 1993). Results in EC (+) of the 4 groups, i.e. FR group, CTR group, FR+BH4 group and CTR+BH4 group are shown in Table 1 below.

TABLE 1

$O_2^-$ production level (100 cpm/mg dry weight)

| Group | Number of cases | Average | Standard deviation |
|---|---|---|---|
| CTR | 4 | 123.1 | 34.5 |
| CTR + BH4 | 4 | 189.3 | 39.2 |
| FR | 4 | 263.6 | 35.9 |
| FR + BH4 | 4 | 118.0 | 24.5 |

As shown in Table 1, FR group showed a significantly high $O_2^-$ production level ($p<0.001$) of twice or more as compared with CTR group in EC (+) when BH4 was not administered, but $O_2^-$ production level in FR group significantly ($p<0.001$) decreased by BH 4 administration. No significant difference was found among the 4 groups in EC (−).

Endothelial NOS Activity

Measurement of eNOS activity was made according to Rees, D. et al., Hypertension 28: 367, 1996. Results in EC (+) of the four groups are shown in Table 2 below.

TABLE 2 eNOS activity (pmol/min/mg protein)

| Group | Number of cases | Average | Standard deviation |
|---|---|---|---|
| CTR | 5 | 63.4 | 13.0 |
| CTR + BH4 | 4 | 57.0 | 8.5 |
| FR | 5 | 22.3 | 10.9 |
| FR + BH4 | 4 | 60.2 | 18.5 |

As shown in Table 2, eNOS activity in FR group was significantly ($p<0.001$) lowered to 50% or less of CTR group when BH4 was not administered, but it was significantly ($p<0.001$) improved by BH 4 administration.

Endothelium-dependent Vasorelaxation

Measurement of endothelium-dependent vasorelaxation was made by the isometric tensiometry (Toda, N. et al., Stroke 24: 1584, 1993) using ink-writing oscillographs (Nippon Kohden Corporation) and a force-displacement transducer (Nippon Kohden Corporation). Data were shown as % maximum relaxation vs. the maximum relaxation induced by $10^{-4}$ M papaverine after aortic sections were partially precontracted with $1-3\times10^{-7}$ M 1-phenylephrine. Endothelium-dependent vasorelaxation induced by acetylcholine ($10^{-5}$M) and calcium ionophore (A23187, Sigma) ($3\times10^{-7}$ M) in EC (+) of each of the 4 groups are shown in Tables 3 and 4, respectively.

TABLE 3

Endothelium-dependent vasorelaxation induced by acetylcholine (% maximum relaxation)

| Group | Number of cases | Average | Standard deviation |
|---|---|---|---|
| CTR | 5 | 89.0 | 3.9 |
| CTR + BH4 | 5 | 92.9 | 2.9 |
| FR | 8 | 65.9 | 6.9 |
| FR + BH4 | 8 | 82.6 | 2.9 |

TABLE 4

| | Endothelium-dependent vasorelaxation induced by calcium ionophore (% maximum relaxation) | | |
|---|---|---|---|
| Group | Number of cases | Average | Standard deviation |
| CTR | 8 | 85.6 | 7.1 |
| CTR + BH4 | 8 | 86.4 | 8.0 |
| FR | 8 | 66.9 | 7.9 |
| FR + BH4 | 8 | 81.8 | 2.7 |

As shown in Tables 3 and 4, endothelium-dependent vasorelaxation induced by acethylcholine and calcium ionophore in FR group was significantly (p<0.001) lowered as compared with CTR group when BH4 was not administered, but it was significantly (p<0.001) recovered by BH 4 administration.

In conclusion, BH4 administration lowered $O^{2-}$ production level, increased eNOS activity and recovered endothelium-dependent vasorelaxation to improve vascular dysfunction in FR group. However, any significant change was not observed in any of these profiles in CTR group even by BH4 administration.

As has been explained, the present invention provides pharmaceutical compositions that effectively prevent and/or improve diseases having vascular dysfunction associated with insulin resistance. In addition, active ingredients of pharmaceutical compositions of the present invention have no danger of side effects or the like even under long-term use because they inherently occur in living bodies.

What is claimed is:

1. A method for preventing or treating diseases having vascular dysfunction associated with insulin resistance, comprising administering to a patient in need thereof a pharmaceutical composition comprising a compound of the formula (I):

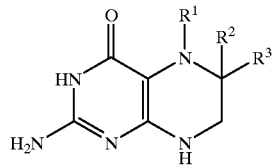

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represents a single bond, or a pharmaceutically acceptable salt thereof.

2. The method for preventing or treating diseases having vascular dysfunction associated with insulin resistance according to claim 1, wherein the disease having vascular dysfunction associated with insulin resistance is a disease with increased production of active oxygen.

3. The method for preventing or treating diseases having vascular dysfunction associated with insulin resistance according to claim 1, wherein the disease having vascular dysfunction associated with insulin resistance is a disease with decreased NO production.

4. The method for preventing or treating diseases having vascular dysfunction associated with insulin resistance according to claim 1, wherein $R^3$ is L-erythro-CH(OH)CH(OH)CH$_3$.

5. The method for preventing or treating diseases having vascular dysfunction associated with insulin resistance according to claim 1, which is for preventing or treating coronary vasoconstrictive angina.

6. The method for preventing or treating diseases having vascular dysfunction associated with insulin resistance according to claim 1, which is for preventing or treating effort angina.

7. The method for preventing or treating diseases having vascular dysfunction associated with insulin resistance according to claim 1, which is for preventing or treating coronary arteriorestenosis following percutaneous transluminal coronary angioplasty (PTCA) or coronary artery bypass grafting (CABG).

8. The method for preventing or treating diseases having vascular dysfunction associated with insulin resistance according to claim 1, which is for preventing or treating arteriosclerosis.

9. The method for preventing or treating diseases having vascular dysfunction associated with insulin resistance according to claim 1, which is for preventing or treating cerebrovascular constrictive lesion.

* * * * *